United States Patent [19]

Markowitz et al.

[11] Patent Number: 5,501,701
[45] Date of Patent: Mar. 26, 1996

[54] PACEMAKER WITH VASOVAGAL SYNCOPE DETECTION AND THERAPY

[75] Inventors: H. Toby Markowitz, Roseville; Michael F. Hess, Minneapolis, both of Minn.

[73] Assignee: Medtronic, Inc., Minneapolis, Minn.

[21] Appl. No.: 309,285

[22] Filed: Sep. 20, 1994

Related U.S. Application Data

[63] Continuation-in-part of Ser. No. 235,433, Apr. 29, 1994, abandoned.

[51] Int. Cl.$^6$ ........................................................ A61N 1/36
[52] U.S. Cl. ........................................................ 607/9
[58] Field of Search .................................. 607/9, 17–19, 607/23, 25

[56] References Cited

U.S. PATENT DOCUMENTS

| | | |
|---|---|---|
| 4,556,063 | 12/1985 | Thompson . |
| 5,119,813 | 6/1992 | Cohen ........................................ 607/17 |
| 5,127,404 | 7/1992 | Wyborny . |
| 5,233,984 | 8/1993 | Thompson ................................. 607/18 |
| 5,284,491 | 2/1994 | Sutton ........................................ 607/17 |
| 5,342,404 | 8/1994 | Alt et al. ..................................... 607/6 |

FOREIGN PATENT DOCUMENTS

| | | |
|---|---|---|
| 9316756 | 9/1993 | WIPO ....................................... 607/17 |

OTHER PUBLICATIONS

Fitzpatrick et al., "Dual Chamber Pacing Aborts Vasovagal Syncope Induced by Head–Up 60° Tilt", PACE vol. 14 Jan. '91.

*Primary Examiner*—William E. Kamm
*Assistant Examiner*—Jeffrey R. Jastrzab
*Attorney, Agent, or Firm*—Michael B. Atlass; Harold R. Patton

[57] ABSTRACT

A method and apparatus for cardiac pacing, in which pacing pulses are provided at an increased rate in response to a detected rapid drop in heart rate. A rapid drop is detected in response to heart rate falling from a persistent rate above a first threshold rate to a stable rate below a second threshold rate. If spontaneous depolarizations are detected while pacing at the increased rate, pacing at the increased rate is terminated.

24 Claims, 5 Drawing Sheets

5,501,701

PACEMAKER WITH VASOVAGAL SYNCOPE DETECTION AND THERAPY

This is a continuation-in-part of application Ser. No. 08/235,433 filed on 29 Apr. 1994, now abandoned.

FIELD OF THE INVENTION

The present invention relates to artificial cardiac pacemakers generally and more particularly to pacemakers for the treatment of patients who experience vasovagal syncope episodes and other effects from vasodepressor or cardioinhibitory disorders, such as carotid sinus syndrome.

BACKGROUND OF THE INVENTION

Vasovagal syncope is a condition marked by a sudden drop in heart rate and blood pressure, resulting in fainting. It is not only unpleasant for a patient, but potentially dangerous, as fainting may lead to injuries from falls. U.S. Pat. No. 5,284,491, issued to Sutton et al. on Feb. 8, 1994 and incorporated herein by reference in its entirety discloses a cardiac pacemaker specifically adapted to treat patients suffering from vasovagal syncope. In particular, the pacer detects when the patient's heart rate drops below a lower "hysteresis" rate and determines whether the average rate of decrease in the patient's heart rate, over a defined number of heartbeats or a defined time interval prior to reaching the "hysteresis" rate, is greater than a preset value. If so, the pacer's rate is set equal to the "hysteresis" rate and thereafter increased to an "intermediate" rate substantially higher than the "hysteresis" rate. The pacer's rate remains at the intermediate" rate for a preset time period and thereafter gradually declines to a lower pacing rate.

SUMMARY OF THE INVENTION

The present invention is directed toward an improved pacemaker for the treatment of patients with vasovagal syncope. The pacemaker of the present invention differs from the prior pacer disclosed in the Sutton patent in that the methods of detection of an episode of vasovagal syncope and the intervention therapy delivered in response are refined. Rather than detecting a rapid rate drop as discussed above in conjunction with the Sutton patent, a persistent rate above a first threshold rate is required to initiate the rate drop detection function, preventing single rapid heartbeats from triggering detection of a rapid rate drop. After detection of a rapid rate drop from above the first threshold rate to a rate below a second threshold rate or "drop rate", a persistent or stable heart rate (e.g. x of y beats less than the drop rate) is required prior to intervention. Criteria for exiting the intervention therapy and for exiting the detection process due to sensed spontaneous depolarizations are also provided.

BRIEF DESCRIPTION OF THE DRAWINGS

The various figures of the drawing are briefly described as follows.

DETAILED DESCRIPTION OF THE PREFERRED EMBODIMENT

Figure 1:
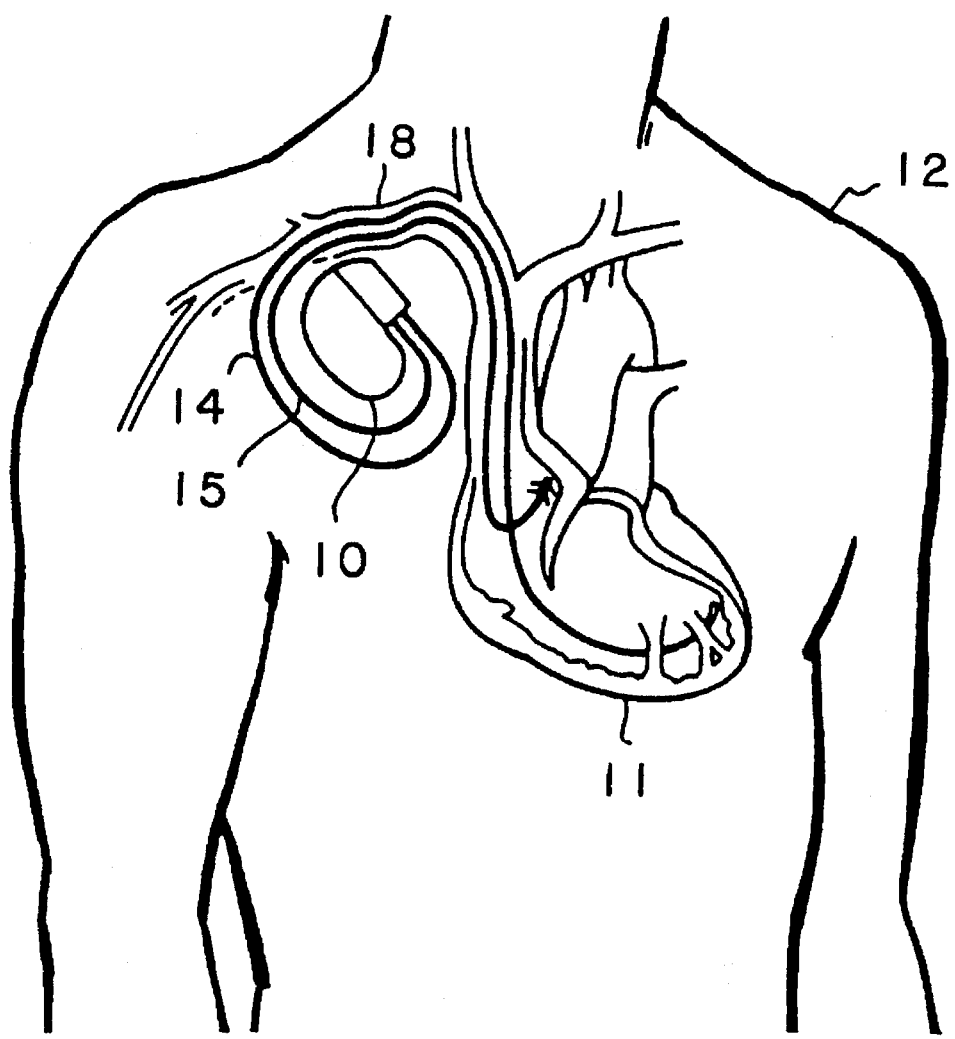
FIG. 1 is a diagram showing the heart of a patient electrically connected to a pacemaker practicing the present invention.

FIG. 1 generally shows a pacemaker 10, of a type suitable for practicing the present invention, implanted in a patient 12. The pacer illustrated is a dual chamber, rate responsive pacemaker, capable of sensing demand for cardiac output and of pacing the atrium and ventricle, but the invention may also be practiced in conjunction with non-rate responsive pacemakers and pacemakers which pace and/or sense in only one chamber of the heart. The pacemaker is provided with leads 14 and 15, which electrically couple the pacemaker 10 to the ventricle and atrium, respectively, of the patient's heart 11 via electrodes located thereon. The electrodes are employed to sense depolarizations of the heart, referred to informally herein as "beats" and to deliver pacing pulses to the heart.

Figure 2:
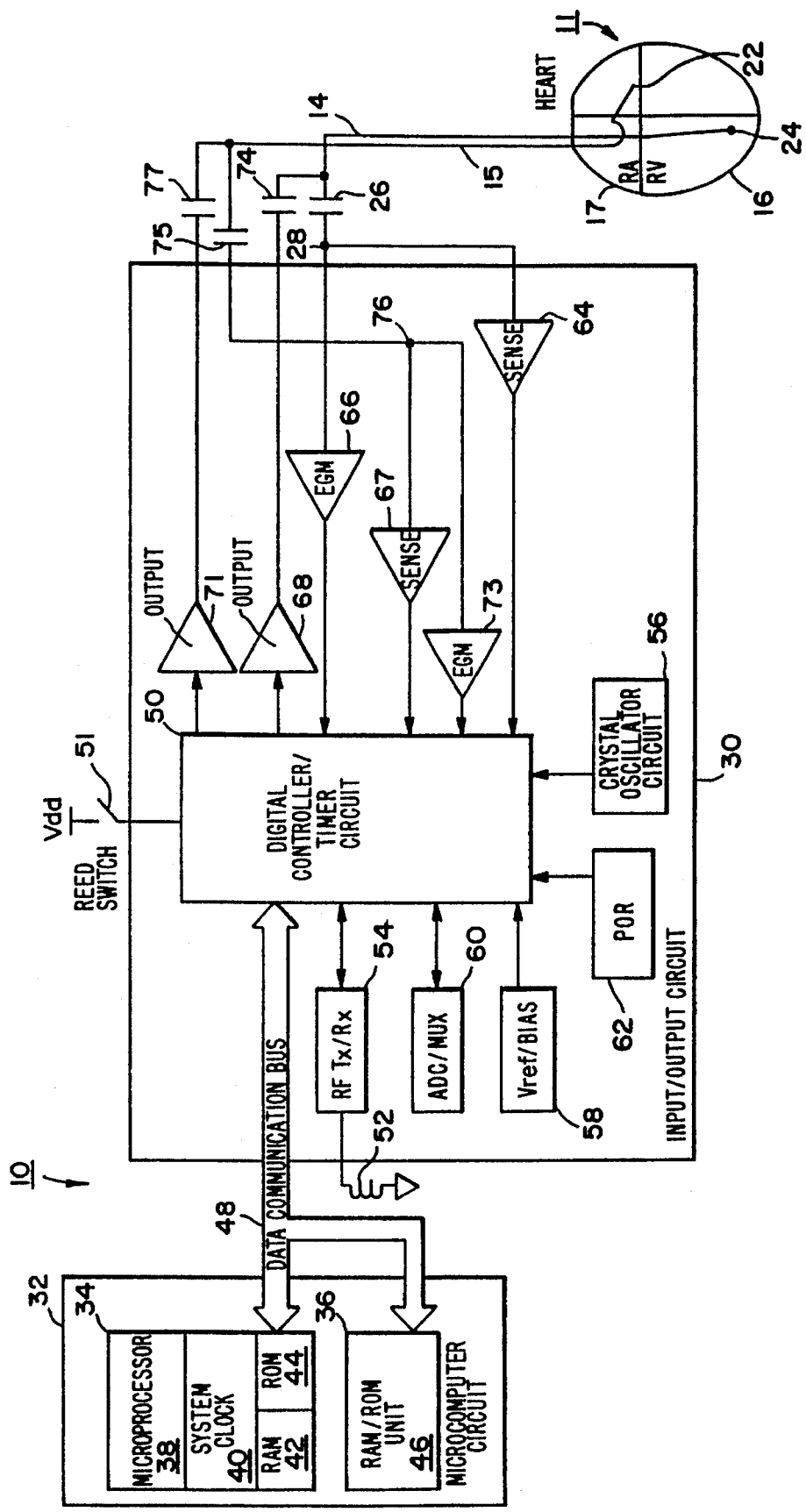
FIG. 2 is a schematic block diagram of an implantable pacemaker in which the present invention may be practiced.

FIG. 2 is a block circuit diagram illustrating a multi-programmable, implantable, dual-chamber, bradycardia pacemaker 10, illustrated in FIG. 1. Although the present invention is described in conjunction with a microprocessor-based architecture, it will be understood by those skilled in the art that it could be implemented in other technology such as digital logic-based, custom integrated circuit (IC) architecture, if desired. It will also be understood that the present invention may be implemented in cardioverters, defibrillators and the like.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14 and 15, as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention, and which is incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired.

Figure 3:
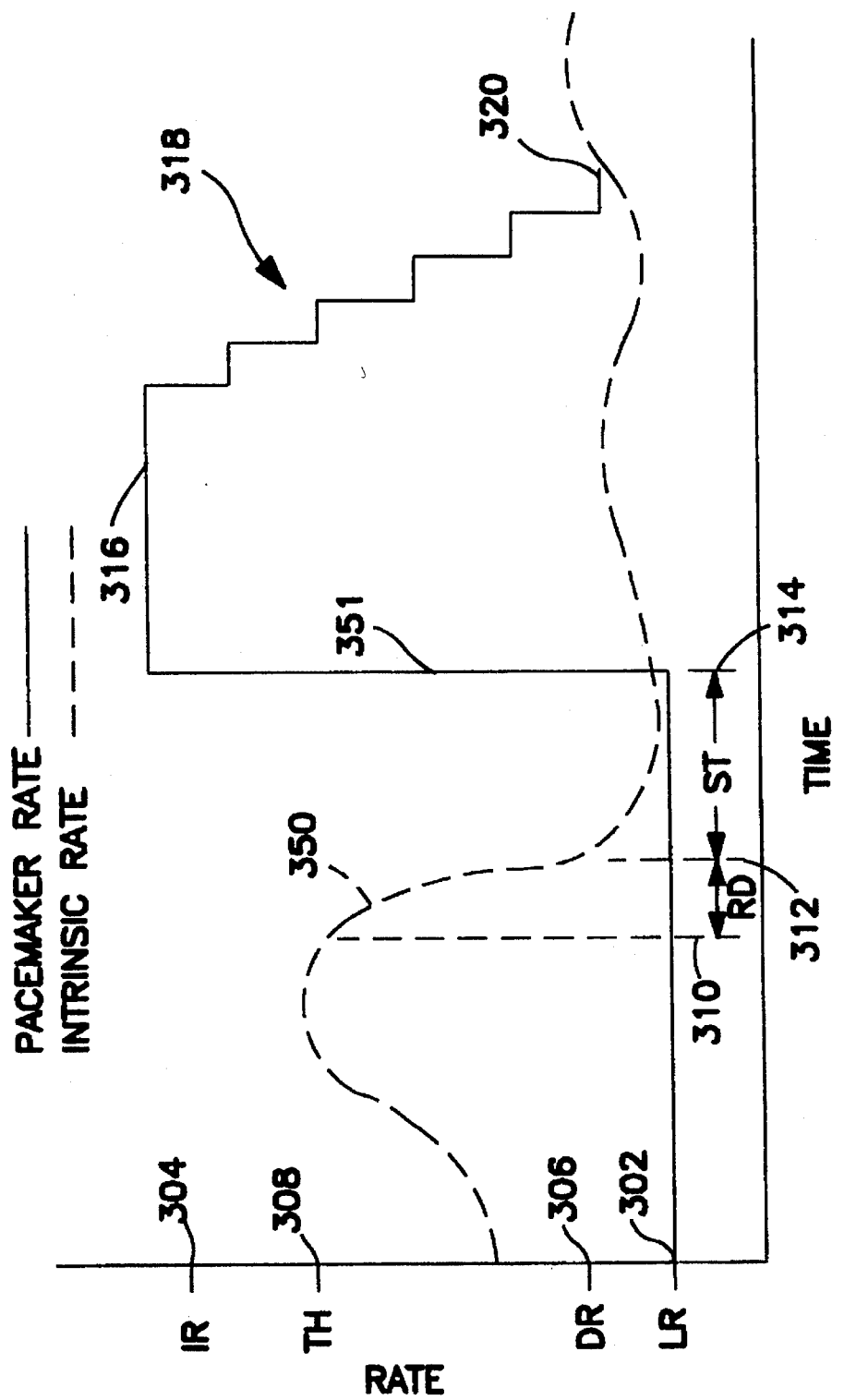
FIG. 3 is a graph of intrinsic heart rates and pacemaker pacing rates versus time, illustrating the operation of a pacemaker practicing the present invention, in response to vasovagal syncope episode.

Details of the vasovagal syncope detection and treatment functions of the present invention are illustrated in FIG. 3. A lower rate (LR, 302) is shown-a rate below which the heart will not be allowed to fall (also known as the base escape rate or the base pacing rate of the pacer). This rate may be, for example, 50–70 beats per minute. Also defined are an intervention rate (IR, 304), substantially above the lower rate, a drop rate (DR, 306), between the lower rate and the intervention rate, and a threshold rate (TH, 308), between the intervention rate and the drop rate. The values of all of these rates are programmable by the physician and it is anticipated that the intervention rate should be less than the maximum pacing rate attainable by the pacer, in the case of rate-responsive or dual chamber (e.g. DDD or VDD) pacers.

The intrinsic heart rate is illustrated by broken line and the pacer's escape rate during is illustrated by solid line. If the invention is practiced in a single chamber pacemaker (e.g. VVI or AAI), the pacer will be inhibited from delivering pulses when the patient's rate is higher than the pacer's escape rate. If the pacer is an atrial synchronized, dual chamber pacer (e.g. DDD or VDD), the pacer will pace synchronized to the patient's intrinsic rate when the patient's rate is higher than the pacer's escape rate. In dual chamber modes which are synchronized to the atrium, it is contemplated that the atrial heart rate will be monitored. For simplicity, it is assumed that the pacer is not set to a rate responsive mode, and that therefore the pacer's escape rate is equal to a fixed lower rate 302.

Detection of a vasovagal syncope episode begins at 310, in response to a series of a predetermined number of sequential heartbeats (e.g. three), above the threshold rate 308. The pacer is then capable of responding to a sudden, significant rate drop, and, in response to the patient's heart rate falling below the threshold rate 308 begins counting the number of heartbeats at rams between the threshold rate 308 and the lower rate 302 or the time elapsed since the heart rate dropped below the threshold rate. At 312, in response to the patient's intrinsic rate being less than the drop rate, so the pacer determines whether the number of beats counted or the elapsed time since the patient's rate fell below the threshold rate is less than or equal to a predetermined value. If not, the pacer determines that the rate decline was gradual, and the escape rate remains at the lower rate 302. As alternatives, following the detection of a persistent heart rate above the threshold, the pacemaker may detect a significant, rapid rate drop by means of a calculation of average rate of change, as discussed above in conjunction with the Sutton patent, or in response to a rate drop of a predetermined magnitude other than the rate difference between the threshold and drop rates, if desired.

If, as illustrated, the pacer determines that the rate drop is both rapid and significant, raising the possibility of an episode of vasovagal syncope, the device thereafter determines whether the patient's rate drop is to a persistent or stable low rate, as opposed to being the result of a single long heartbeat interval as might happen following a premature atrial contraction, if the atrial rate is being tracked, or following a premature ventricular contraction, if the ventricular rate is being tracked. The heartbeats including the first beat below the drop rate 306 are monitored, and if a predetermined proportion of these beats (e.g. 3 of 8, 4 of 5, etc.) are less than the drop rate, the occurrence of a vasovagal syncope episode is confirmed, as illustrated at 314, and therapeutic intervention is triggered. Otherwise, the pacer's escape rate remains at the lower rate and the pacer awaits the next occurrence of a persistent rate above the rate threshold.

The therapeutic intervention as illustrated is provided by increasing the pacer's escape rate to the intervention rate 304, at 316. In the absence of faster spontaneous heart rates, the escape rate remains at the intervention rate for a programmed period of time and thereafter gradually declines at 318 until the spontaneous heart rate exceeds the pacer's escape rate at 320, at which point the pacer's escape rate is reset to the lower rate. If the patient's spontaneous rate exceeds the intervention rate, the pacer similarly resets its escape rate to the lower rate, and aborts the therapeutic intervention.

Figure 4:
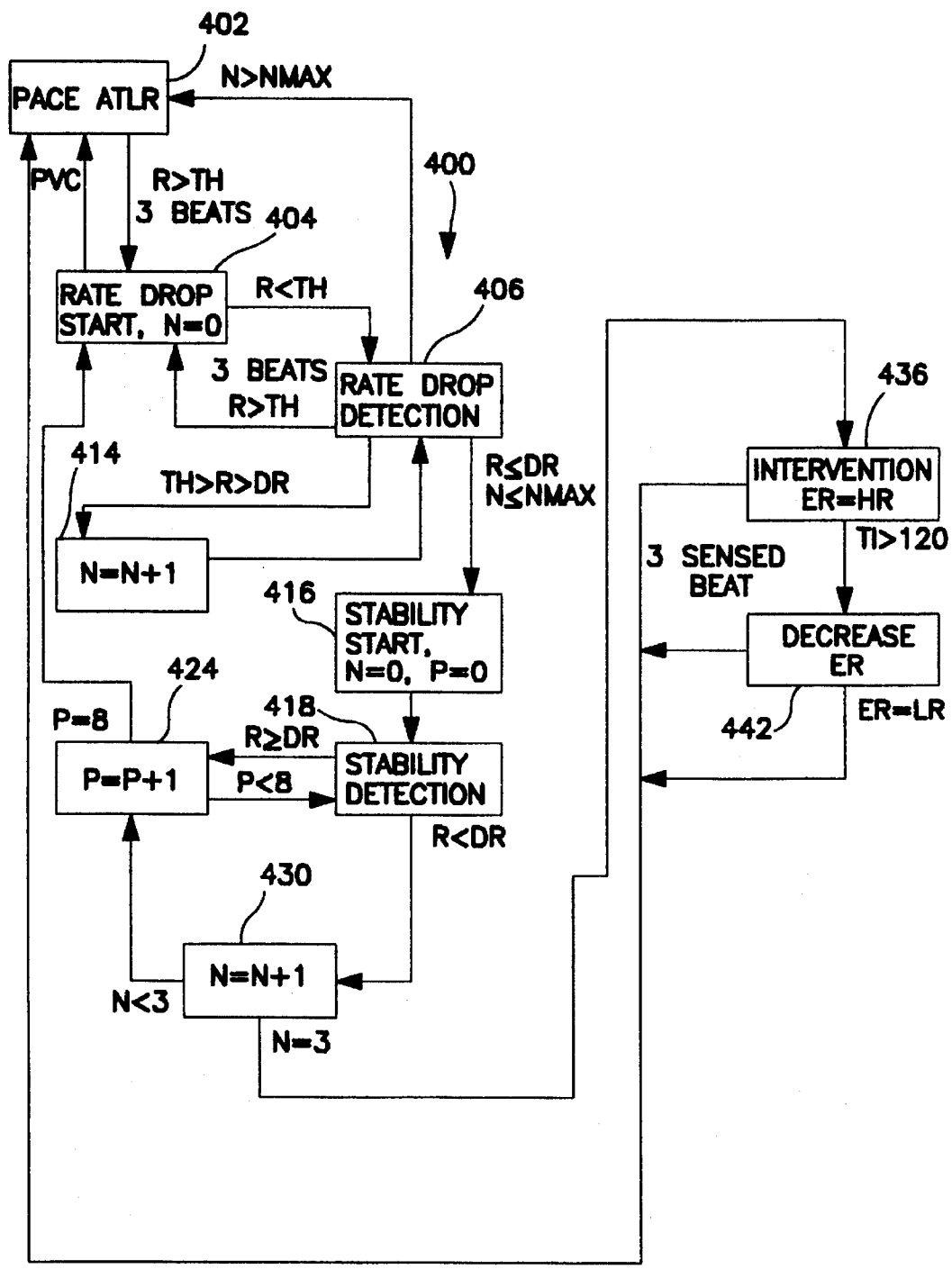
FIG. 4 is a flowchart illustrating the functional operation of a pacemaker practicing the present invention.

The flowchart of FIG. 4 illustrates the operation of the microprocessor 34 (FIG. 2) in implementing present invention in more detail. For purposes of interpreting the flow chart, it should be understood that the device is operating in DDD mode, and that the various heart rates referred to are defined by intervals between adjacent sensed and paced atrial depolarizations, preferably including sensed atrial depolarizations during and outside of atrial refractory periods. An individual heartbeat or depolarization in this context has a rate equal to the reciprocal of the interval separating it from the preceding depolarization.

Normally, at 402, the vasovagal syncope detection function is in an idle state, and the pacemaker paced in DDD mode with the escape rate set equal to the lower rate (LR) and the microprocessor keeping track of beats above the threshold rate (TH). The threshold rate TH is chosen according to the needs of the patient, perhaps in the range of 70 to 90 BPM, for example. In response to detection of a predetermined number of successive beats above the threshold rate, the rate drop detection function is activated at 404, and the microprocessor sets the beat count "N" to zero and awaits a heartbeat having a rate less that the threshold rate. In devices programmed to the VDD or DDD mode, if desired, desired, occurrence of a premature ventricular contraction (PVC) prior to an atrial heartbeat below the threshold rate (TH) may return the vasovagal syncope detection function to the idle state at 402.

In response to a heartbeat having a rate less than the threshold rate, the processor initiates rate drop detection at 406 and sets N equal to one, and the rate of subsequent beats is monitored. Each beat thereafter falling between the threshold rate (TH) and the lower rate (LR) causes "N" to be incremented at 414. If "N" is incremented above a preset count "NMAX", prior to a beat at a rate less than the drop rate (DR), the processor returns the vasovagal syncope detection function to the idle state at 402. If three consecutive beats above the threshold rate are sensed prior to a beat at a rate less than the drop rate (DR), the processor returns the vasovagal syncope detection function to the starting state at 404, resetting "N" to zero.

Occurrence of a beat having a rate lower than the drop rate, prior to either "N" exceeding "NMAX" or the occurrence of three beats above the threshold rate (TH), triggers the microprocessor to initiate the stability detection function at 416. The value of "N" is rest to zero, along with the value of a second count "P", and stability detection is begun at 418. The processor monitors the rate of heartbeats thereafter, and increments the count "P" at 424 for each beat above or equal to the drop rate and increments the count "N" at 430 for each beat below the drop rate, including the first beat below the drop rate which initiated the stability detection function. If "N" reaches three before "P" reaches eight, therapeutic intervention is triggered at 436. If "P" reaches eight, the processor returns the vasovagal syncope detection function to the idle state at 402 and awaits three subsequent beats above the threshold rate (TH).

If therapeutic intervention is triggered at 436, the processor sets the controller/ timer circuit 50 (FIG. 2) to define an escape rate equal to the intervention rate (IR), e.g. 70–100 bpm, and initiates a programmed intervention rate time period, e.g. two minutes. If, during this period, the atrial rate exceeds the intervention rate (IR), indicated, for example by three successive sensed atrial depolarizations, the processor aborts the therapeutic intervention, returns the vasovagal syncope function to the idle state and resets the escape rate to equal the lower rate at 402.

Following the intervention rate time period, the processor regularly decrements the escape rate during a fallback period at 442. Rate is decremented periodically until either the escape rate reaches the lower rate or until the intrinsic atrial rate exceeds the current escape rate, indicated, for example by three successive sensed atrial depolarizations. The processor then sets the escape rate equal to the lower rate and returns the vasovagal syncope detection function to the idle state at 402.

Figure 5:
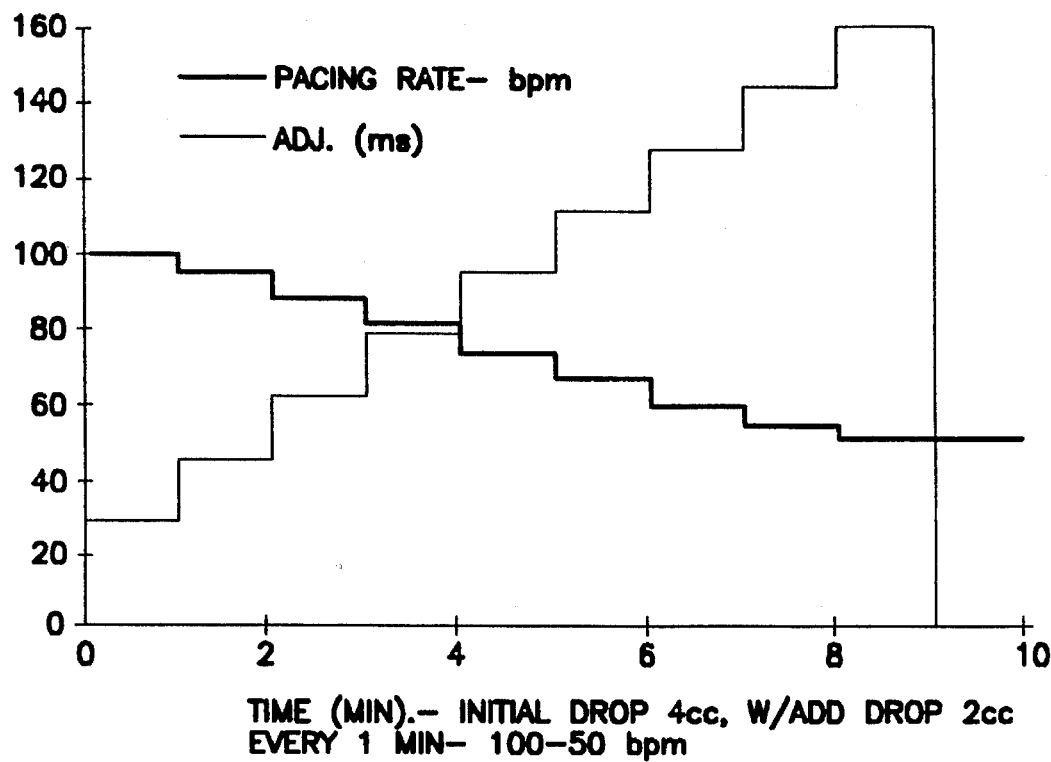
FIGS. 5 and 6 are examples of pacing rate deceleration patterns after pacing at an intervention rate.
Figure 6:
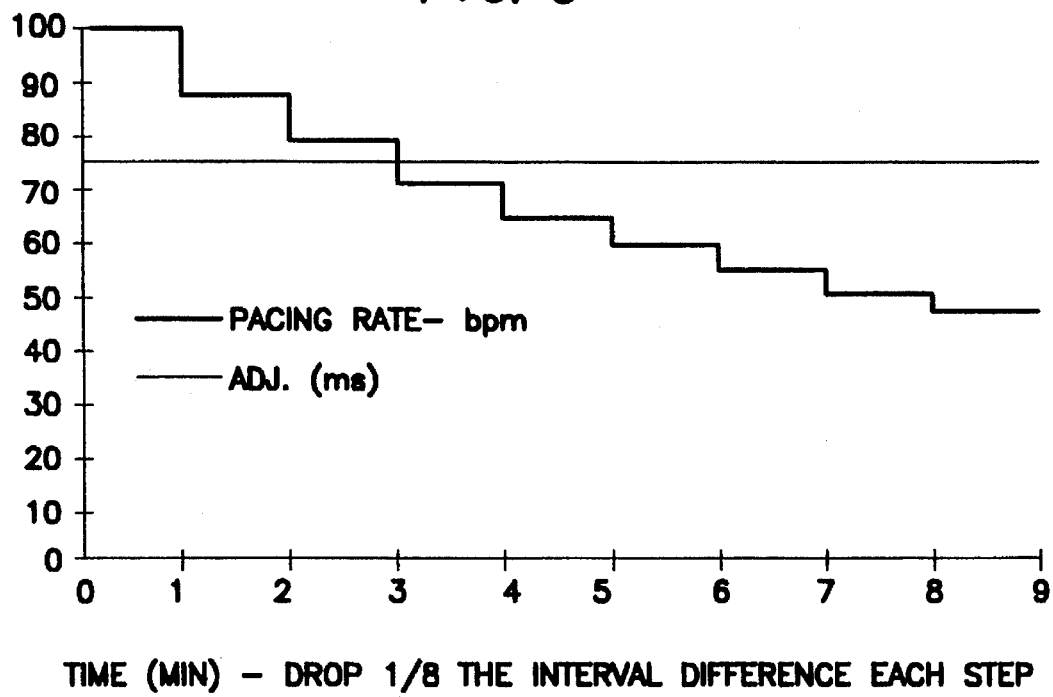

FIGS. 5 and 6 show two examples of sequential rate reductions during fallback to the threshold rate which are suitable for use in the present invention. The escape rate in FIG. 5 is decremented by predetermined rate decrements each minute until the lower rate (LR) is reached. The escape rate in FIG. 6 is decremented once every minute by incrementing the pacing escape by interval one-eighth of the difference between the escape interval at the intervention rate and the escape interval at lower rate, until the threshold rate TR is reached.

Variations and modifications to the present invention are possible given the above disclosure. However, such variations and modifications are intended to be within the scope of the invention claimed by this letters patent. For example, although the preferred embodiment is directed to detection and treatment with respect to vasovagal syncope, the present invention can also be used with respect to neurogenic syncope, vasodepressor and cardioinhibitory disorders, such as carotid sinus syndrome.

We claim:

1. A cardiac pacer comprising:

means for detecting depolarizations of a heart and generating signals therefrom;

means for determining an intrinsic heart rate connected to receive said signals from such detected depolarization;

pulse generating means for delivering cardiac pacing pulses at a first pacing rate;

means for defining first and second threshold heart rates;

drop detecting means for detecting a rapid drop in spontaneous heart depolarization rate from a rate above said first threshold heart rate to a rate below said second threshold heart rate.

2. A cardiac pacer comprising:

means for detecting depolarizations of a heart;

means for determining an intrinsic heart rate from such detected depolarization;

pulse generating means for delivering cardiac pacing pulses at a first pacing rate;

means for defining first and second threshold heart rates;

drop detecting means for detecting a rapid drop in spontaneous heart depolarization rate from a rate above said first threshold heart rate to an rate below said second threshold heart rate and comprising means for detecting a persistent heart depolarization rate above said first threshold heart rate and means for detecting a rapid drop in spontaneous heart depolarization rate from said persistent heart rate above said first threshold heart rate to a rate below said second threshold heart rate.

means responsive to said detected rapid drop in spontaneous heart depolarization rate for causing said pulse generator means to deliver pacing pulses at a second pacing rate higher than said first pacing rate.

3. A cardiac pacer according to claim 2 wherein said means for detecting a persistent heart depolarization rate comprises means for detecting a sequence of a predetermined number of heart depolarizations above said first threshold heart rate.

4. A cardiac pacer according to claim 1 wherein said drop detecting means comprises means for detecting a stable heart depolarization rate below said second threshold heart rate and means for detecting a rapid drop in spontaneous heart depolarization rate from a rate above said first threshold heart rate to a stable rate below said second threshold heart rate.

5. A cardiac pacer according to claim 4 wherein said means for detecting a stable heart depolarization rate below said second threshold heart rate comprises means for detecting a predetermined proportion of heart depolarizations having rates less than said second threshold rate.

6. A cardiac pacer comprising:

means for detecting heart depolarizations and for generating signals therefrom;

means for determining an intrinsic heart rate connected to receive said signals from such detected depolarizations;

pulse generating means for delivering cardiac pacing pulses at a first pacing rate;

means for defining a threshold heart rate;

drop detecting means for detecting a rapid drop in spontaneous heart depolarization rate from a rate above said threshold heart rate.

7. A cardiac pacer comprising:

means for detecting heart depolizations;

means for determining an intrinsic heart rate from such detected depolarizations;

pulse generating means for delivering cardiac pacing pulses at a first pacing rate;

means for defining a threshold heart rate;

drop detecting means for detecting a rapid drop in spontaneous heart depolarization rate from a rate above said threshold heart rate comprising means for detecting a persistent heart depolarization rate above said threshold heart rate and means for detecting a rapid drop in spontaneous heart depolarization rate from said persistent heart depolarization rate above said threshold heart rate;

means responsive to a said detected rapid drop in spontaneous heart depolarization rate for causing said pulse generator means to deliver pacing pulses at a second pacing rate higher than said first pacing rate.

8. A cardiac pacer according to claim 7 wherein said means for detecting a persistent heart depolarization rate comprises means for detecting a sequence of a predetermined number of heart depolarizations above said threshold heart rate.

9. A cardiac pacer comprising:

means for detecting heart depolarizations;

pulse generating means for delivering cardiac pacing pulses at a first pacing rate;

means for defining a threshold heart rate;

means for detecting a rapid rate drop comprising; means for detecting a stable heart depolarization rate below said threshold heart rate, and means for detecting a rapid drop in spontaneous heart depolarization rate to a stable rate below said threshold heart rate, said means for detecting a stable heart depolarization rate below said threshold heart rate comprising means for detecting a predetermined proportion of heart depolarizations having rates less than said threshold rate to heart depolarizations having a rate greater than said threshold rate; and means for causing said pulse generating means to deliver pacing pulses at a second pacing rate, higher than said first pacing rate, responsive to a said detected rapid rate drop.

10. A cardiac pacer comprising:

means for detecting heart depolarizations;

pulse generating means for delivering cardiac pacing pulses at a first pacing rate;

drop detecting means for detecting a rapid drop in spontaneous heart depolarization rate;

means responsive to a said detected rapid drop in spontaneous heart depolarization rate for causing said pulse generator means to deliver pacing pulses at a second pacing rate instead of and higher than said first pacing rate;

means responsive to detected heart depolarizations while said pulse generating means is delivering pacing pulses at said second pacing rate, for causing said pulse generating means to generate pulses at said first pacing rate.

11. A cardiac pacer according to claim 10, wherein;

said means for causing said pulse generator means to deliver pacing pulses at a second pacing rate comprises means for causing said pulse generator means to deliver pacing pulses at a second pacing rate for a defined time interval, and wherein said pacer further comprises:

means for causing said pulse generating means to deliver pacing pulses at a sequence of pacing rates gradually decreasing from said second pacing rate to said first pacing rate, after said defined time interval; and means responsive to detected heart depolarizations while said pulse generating means is delivering pacing pulses at said sequence of pacing rates, for causing said pulse generating means to generate pulses at said first heart rate.

12. A cardiac pacer according to claim 11 wherein said means responsive to detected heart depolarizations while said pulse generating means is delivering pacing pulses at said sequence of pacing rates comprises means responsive to a sequence of a defined number of heart depolarizations.

13. A cardiac pacer according to claim 10 wherein said means responsive to detected heart depolarizations while said pulse generating means is delivering pacing pulses at said second pacing rate comprises means responsive to a sequence of a defined number of heart depolarizations.

14. A method of cardiac pacing; comprising:

detecting depolarizations of a heart delivering cardiac pacing pulses at a first pacing rate;

defining first and second threshold heart rates;

detecting a rapid drop in spontaneous heart depolarization rate from a rate above said first threshold heart rate to a rate below said second threshold heart rate based on said detected heart depolarizations; and responsive to a said detected rapid drop in spontaneous heart depolarization rate delivering pacing pulses at a second pacing rate higher than said first pacing rate.

15. A method according to claim 14 wherein said drop detecting step comprises detecting a persistent heart depolarization rate above said first threshold heart rate and detecting a rapid drop in spontaneous heart depolarization rate from said persistent heart rate above said first threshold heart rate to a rate below said second threshold heart rate.

16. A method according to claim 15 wherein said step of detecting a persistent heart depolarization rate comprises detecting a sequence of a predetermined number of heart depolarizations above said first threshold heart rate.

17. A method according to claim 14 wherein said drop detecting step comprises detecting a stable heart depolarization rate below said second threshold heart rate and detecting a rapid drop in spontaneous heart depolarization rate from a rate above said first threshold heart rate to a stable rate below said second threshold heart rate.

18. A method according to claim 17 wherein said step of detecting a stable heart depolarization rate below said second threshold heart rate comprises detecting a predetermined proportion of heart depolarizations having rates less than said second threshold rate.

19. A method of cardiac pacing, compromising:

detecting heart depolarizations;

delivering cardiac pacing pulses at a first pacing rate;

defining a threshold heart rate;

detecting a rapid drop in spontaneous heart depolarization rate from a rate above said threshold heart rate based on said detected heart depolarizations; and responsive to said detected rapid drop in spontaneous heart depolarization rate, delivering pacing pulses at a second pacing rate higher than said first pacing rate.

20. A method according to claim 19 wherein said drop detecting step comprises detecting a persistent heart depolarization rate above said threshold heart rate and detecting a rapid drop in spontaneous heart depolarization rate from said persistent heart depolarization rate above said threshold heart rate.

21. A method according to claim 20 wherein said step of detecting a persistent heart depolarization rate comprises detecting a sequence of a predetermined number of heart depolarizations above said threshold heart rate.

22. A method of cardiac pacing, comprising:

detecting heart depolarizations;

delivering cardiac pacing pulses at a first pacing rate;

defining a threshold heart rate;

detecting a stable heart depolarization rate below said threshold heart rate in response to detecting a predetermined proportion of heart depolarizations having rates less than said threshold rate to heart depolarizations having a rate greater than said threshold rate;

detecting a rapid drop in spontaneous heart depolarization rate to a stable rate below said threshold heart rate; and in response to detecting a said rapid drop, delivering pacing pulses at a second pacing rate higher than said first pacing rate.

23. A method of cardiac pacing, compromising:

detecting heart depolarizations;

delivering cardiac pacing pulses at a first pacing rate;

detecting a rapid drop in spontaneous heart depolarization rate;

responsive to said detected rapid drop in spontaneous heart depolarization rate, delivering pacing pulses at a second pacing rate instead of and higher than said first pacing rate;

responsive to detected heart depolarizations while delivering pacing pulses at said second pacing rate, delivering pacing pulses at said first pacing rate.

24. A method according to claim 23, wherein;

said step of delivering pacing pulses at a second pacing rate comprises delivering pacing pulses at said second pacing rate for a defined time interval, and wherein said method further comprises:

delivering pacing pulses at a sequence of pacing rates gradually decreasing from said second pacing rate to said first pacing rate, after said defined time interval; and responsive to detected heart depolarizations while delivering pacing pulses at said sequence of pacing rates, delivering pacing pulses at said first heart rate.

* * * * *